United States Patent
Mader et al.

(10) Patent No.: US 6,914,677 B2
(45) Date of Patent: Jul. 5, 2005

(54) DEVICE AND METHOD FOR OPTICALLY MEASURING THE CONCENTRATION OF A SUBSTANCE

(75) Inventors: Lutz Mader, Dresden (DE); Thomas Böhme, Dürröhrsdorf-Dittersbach (DE); Matthias Lau, Dresden (DE); Ulrich Künzelmann, Dresden (DE)

(73) Assignee: Sentronic GmbH Gesellschaft fur Optische Messsysteme, Dresden (DE)

( * ) Notice: Subject to any disclaimer, the term of this patent is extended or adjusted under 35 U.S.C. 154(b) by 0 days.

(21) Appl. No.: 10/416,845
(22) PCT Filed: Nov. 17, 2001
(86) PCT No.: PCT/DE01/04362
§ 371 (c)(1),
(2), (4) Date: Jul. 1, 2003
(87) PCT Pub. No.: WO02/40972
PCT Pub. Date: May 23, 2002

(65) Prior Publication Data
US 2004/0114137 A1 Jun. 17, 2004

(30) Foreign Application Priority Data
Nov. 18, 2000 (DE) .................................. 100 58 579

(51) Int. Cl.$^7$ .............................................. G01N 21/25
(52) U.S. Cl. .................. 356/417; 250/458.1; 422/82.08
(58) Field of Search ........... 356/417; 250/458.1–461.2; 422/82.08

(56) References Cited

U.S. PATENT DOCUMENTS

| 4,599,307 A | * | 7/1986 | Saunders et al. | ......... | 250/461.2 |
| 4,632,807 A | * | 12/1986 | Marsoner | ................. | 422/82.08 |
| 5,039,490 A | * | 8/1991 | Marsoner et al. | ......... | 422/82.01 |
| 5,525,466 A | * | 6/1996 | Slovacek et al. | ......... | 422/82.05 |
| 5,856,203 A | * | 1/1999 | Robinson et al. | ......... | 422/82.05 |
| 6,320,196 B1 | * | 11/2001 | Dorsel et al. | ............. | 250/458.1 |

FOREIGN PATENT DOCUMENTS

| WO | WO 00/13003 A | 3/2000 |
| WO | WO 00/29820 A | 5/2000 |

OTHER PUBLICATIONS

Bruno et al., "All–Solid–State Miniaturized Fluorescence Sensor Array for the Determination of Critical Gases and Electrolytes in Blood," Anal. Chem., 69, 507–513 (1992).

* cited by examiner

Primary Examiner—F. L. Evans
Assistant Examiner—Kara Geisel
(74) Attorney, Agent, or Firm—Leydig, Voit & Mayer, Ltd.

(57) ABSTRACT

The invention relates to a device and a method for optically measuring the concentrations of a substance contained in a fluid medium. With the solution according to the invention the accuracy of measurement is to be increased in accordance with the object over a greater period without any additional calibration measurements, and ageing of a fluorescent substance within a layer is to be taken into consideration, in particular, and the long-time drift of such a measurement system is to be reduced. To achieve this, a layer containing such a known fluorescent substance or layer system are employed in which fluorescence is excited. The fluorescence changes depending on a substance concentration or a pH-value, and the intensity varying correspondingly in time or phase shift of the fluorescent light is allowed to be measured with at least one optical detector with the known intensity or phase of the fluorescence exciting light. On that occasion, the exciting light is directed upon at least two areas being optically separated from each other of a layer containing a fluorescent substance or two equal layers each having a different excitation energy during the useful life, and measured values of fluorescence intensity, fluorescence decay times or phase shifts being locally and/or timely separated of both areas or layers are fed to an electronic comparative and correction value determination unit.

18 Claims, 1 Drawing Sheet

DEVICE AND METHOD FOR OPTICALLY MEASURING THE CONCENTRATION OF A SUBSTANCE

Figure 1:
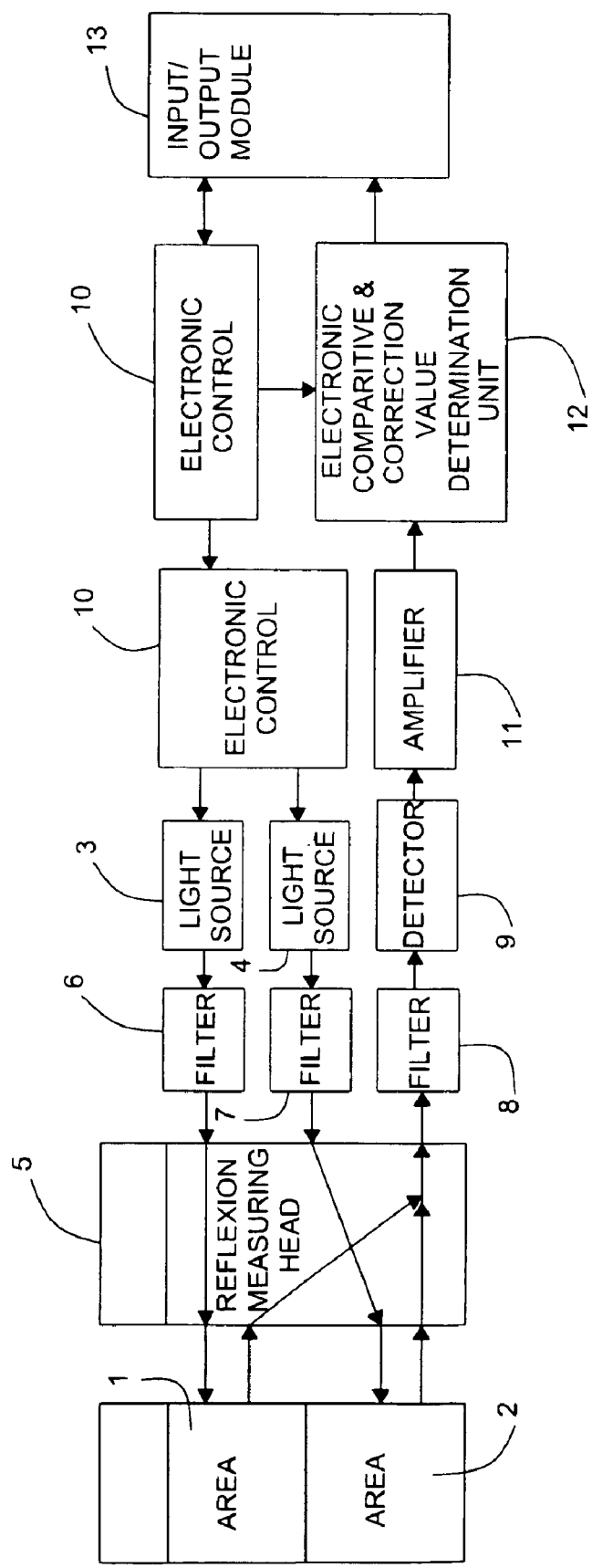

This application is the U.S. national phase of international patent application PCT/DE01/04362, filed on Nov. 17, 2001, and claiming priority to German patent application number 10058579.5, filed Nov. 18, 2000, all of which are hereby incorporated by reference.

The invention relates to a device and a method for optically measuring the concentrations of a substance contained in a fluid medium, and herein in particular the measurement of the oxygen concentration and partial pressure of oxygen, respectively, and the carbon dioxide or nitrate concentrations in gas mixtures (e.g. air) or liquids. However, it is also allowed to determine the pH-value of a fluid. Use in the chemical sensory analysis or with biological fluorescence labels As possible as well.

On that occasion, the well-known phenomenon of the quenching of fluorescence of a fluorescent substance is utilized which occurs in a more or less strong manner depending on such a substance concentration.

Such fluorescent substances such as known ruthenium complexes are embedded in an array, and form a respective sensitive layer in which fluorescence is excited during the radiation with light of a selected wavelength. With a known constant intensity of the exciting light the intensity of fluorescence can be measured with optical detectors.

If a layer containing such a fluorescent substance contacts with a fluid medium which contains oxygen, for example, then depending on the respective oxygen concentration and its partial pressure, respectively, the intensity of fluorescence is decreased such that a reduced level of the test signal is available at the output of an optical detector measuring the intensity of fluorescence, and this reduction can be utilized as a dimension for the oxygen concentration, for example.

However, with such fluorescent layers, the intensity of fluorescence decreases in the course of time with measurement conditions as such being held constantly, in particular with the same conditions of excitation of fluorescence. Usually, this is denoted as ageing and long-time drift of such layers, respectively. For this reason, the useful life of such fluorescent layers is limited in time accordingly, and they have to be replaced by new sensitive layers in more or less great intervals.

Thus, during the life time and service life, respectively, the measuring sensitivity varies (such decreasing the measuring sensitivity as a rule), and it occurs a time varying error of measurement since with a constant excitation power, thus with the intensity of the exciting light held constantly, the measurable intensity of fluorescence is reduced. However, this reduction of the intensity of fluorescence as a result of ageing does not proceed in a linear or proportional manner, but with more or less long lasting measurement breaks, in particular, such recreation effects also occur which cannot readily be taken into consideration by means of conventional correction procedures having constant correction factors, for example.

However, for many cases of application to determine the substance concentrations it does not merely depend on a good response characteristic in a short time but it depends on the possibilities for continuously measuring during over longer periods, as well. However, as already explained above, since the signal level reduces and changes due to ageing without changing the concentration of the respective substance accordingly, it is required until now to frequently carry out expensive calibration measurements in short time intervals such that measurement breaks are necessary.

To counteract the descent of the intensity of fluorescence in such a layer during the time life, it is not a probate means to increase the intensity of excitation and excitation power, respectively, of the light used for the excitation of fluorescence, and rather can result in reducing the useful life of such fluorescent layers or fluorescent substances in a disadvantageous form.

Hence, it is an object of the invention to provide a device and a method wherein the accuracy of measurement is allowed to be increased during a longer period without any additional calibration measurements.

This object preferably is achieved by the characterizing features of the present invention. Advantageous embodiments and further developments of the solution will be apparent from the description of the invention provided herein.

With the solution according to the invention, based on that known, a layer containing a fluorescent substance or layer system is used which will be irradiated with light having a wavelength being able for the fluorescent substance to be excited, and this layer is in contact with the fluid medium in which the respective substance concentration and an oxygen concentration, in particular, are to be determined.

To achieve this, at least one suitable light source, e.g. a luminescence diode or laser diode is used by means of which the excitation of fluorescence takes place at a predetermined light intensity and excitation power. The excited fluorescence is measured with at least one optical detector. On that occasion, excitation of fluorescence is excited within at least two areas being optically separated from each other or two layers being optically separated from each other, accordingly, which can be brought about either with two suitable light sources or with interconnecting an optical beam splitter, a Y-type distributor or optical fibers having merely one such light source. If two light sources are used, these will be adjusted and regulated, respectively, and the luminous radiation will be arranged such that the light impinging upon the layer has the same intensity and power for excitation of fluorescence.

However, it is also possible to determine the behaviour of decay time of the fluorescent light influenced accordingly after switching off such as in a pulsed manner the light sources for the excitation of fluorescence.

Another alternative is in the determination of an occurring phase shift of the fluorescent light.

However, in the following, it is merely to be dealt with the measurement of intensity by way of example in more detail, wherein it is only to be dealt with the influence of the different excitation energies as well by means of different excitation times in which fluorescence is to be excited in the areas or layers, and it remains open the possibility to use the excitation energy by means of influencing the excitation energy, as well.

The two areas or layers being optically separated from each other can also be denoted as channels wherein such a channel is concerned with a measuring channel and the other is concerned with a correction channel.

The area illuminated for the measuring channel or this layer is applied with a greater excitation energy during the total useful life than it is the case for the area or the layer which is used for the correction channel.

Since the excitation power is to be held equally and constantly, as previously mentioned, advantageously the excitation time can be reduced in the correction channel in comparison with the corresponding excitation time in the measuring channel. Advantageously, this can be achieved by means of the reduction of the excitation time. In practice, at least the area and the layer, respectively, which are used for the correction channel are periodically irradiated with exciting light, and there are breaks between the excitation periods in which no excitation of fluorescence is taking place.

The excitation of fluorescence in the measuring channel can be provided in a continuous form but also in an intermittent form wherein the excitation breaks for the measuring channel are smaller than the breaks for the correction channel such that the excitation energy over the useful life for the correction channel is less, such that the level of the measured value for this channel decreases in a less strong manner than being the case in the area and layer, respectively, having the function as a measuring channel.

The excitation energy and excitation times, respectively, for the correction channel should be $\leq 50\%$, preferably $\leq 8\%$ than for the measuring channel.

The exciting light of the one light source and also the at least two light sources, respectively, can be directed through suitable optical elements such as e.g. lenses and filters, through optical fibers upon the respective areas and layers, respectively, as well.

The excited fluorescent light can be measured with an optical detector for the two areas and layers, respectively, wherein the fluorescent light from the respective area and layer, respectively, is directed upon the one optical detector by means of corresponding suitable optical elements, as well. In this case it is advantageous to alternatingly provide the exitation of fluorescence in rotation in the two areas and layers, respectively, wherein the illumination times for the area and this layer, respectively, used as measuring channel are already greater than for the other area and the other layer each, respectively.

If a separate optical detector is used for each of the two optically separated areas and the optically separated layers, respectively, each the two areas and layers, respectively, are allowed to be simultaneously irradiated with exciting light at particular times, and consequently fluorescent light can be excited there. The irradiation times, and consequently the times as well in which fluorescence is excited are greater in each case, in the cumulated form for the area and the layer, respectively, which represent the measuring channel than being the case for the corresponding other area and other layer, respectively, such that the desired difference of exitation energy will be achieved during the useful life of the layers.

The measured values of the intensity of fluorescence which are measured with the one or at least two optical detectors as well are allowed to be fed either in parallel or sequentially to an electronic comparative and correction value determination unit wherein the function, effect and processing of the test signals is still to be explained later in more detail.

In addition to the already mentioned possibility of preferably switching on and switching off in an electronic manner the light sources used for the excitation of fluorescence during time intervals, which can be predetermined, this can also take place in that the optical path of the exciting light will be stopped over time intervals which can be predetermined as well such that no exciting light passes upon the layer containing the fluorescent substance during particular time intervals. To achieve this, electric or optoelectronic, purely optical switches and mechanically movable components, respectively, can be utilized. Thus, for example, a so called chopper can be located between the light sources and light exit apertures and the layer, respectively. A chopper wheel comprises sections, openings or apertures which permit the illumination of a particular area of the layer at a constant speed of such a chopper wheel, and a light barrier is formed at particular different angular positions, wherein it can be sufficient to utilize a chopper wheel being correspondingly formed and arranged for the measuring channel and the correction channel.

However, it is also allowed to use an optical filter of a similar form wherein at least the intensity and excitation power, respectively, can be reduced for a time such that the influence of the different excitation energies as desired according to the invention thus can also be achieved.

By influencing the excitation energy during the useful life of the layers, ageing and long-time drift, respectively, can be compensated to increase the accuracy of measurement since the area used for the correction channel and this layer, respectively, are ageing substantially more slowly, and corresponding less drifts of measured values are occurring there.

Subsequently, the processing of measured values in an electronic determination unit of comparative and correction values will be explained by way of example, wherein in particular this explanation applies to a device and a method, respectively, in which merely an optical detector is preferably utilized, and a measurement of intensity is carried out.

On that occasion, the illumination that is to say the excitation of fluorescence in the areas and layers, respectively, for the measuring channel and the correction channel should be performed for time-division multiplex. This means, that fluorescence will always be excited only in one of the two each areas and layers, respectively, and at the same time the other area and these layers, respectively, will not be excited. The area used for the measuring channel and the layer, respectively, will be irradiated with exciting light within a time interval by a correction grade g being longer than the area and the layer, respectively, which is used for the correction channel. This correction grade g should be selected such that the reduction of the signal-to-noise ratio is disregarded in comparison with conventional one-channel type measurement systems. On that occasion, for the signal-to-noise ratios SNR applies:

$$SNR' = SNR * \sqrt{\frac{g}{g+1}} \approx SNR$$

The response times of the two channels are equal. The optical separation can be obtained by sufficiently great distances of the illuminated areas under consideration of the apertures of the exciting light, however, by means of the optical barrier layers, as well.

For the evaluation of ageing of the layers the following model can be earmarked.

The measured values of the measuring and correction channels are each composed of the portion of the substance concentration, a portion depending on ageing and a constant offset as well. The sum of errors involves optical and electric cross-talk effects, and an blind value of the layer depending on ageing as well. For the determination of the oxygen concentration applies:

$$F(C\ O_2,t)=A(t)*F(C\ O_2)+\text{Offset}$$

wherein are

F=fluorescence

A=ageing $C\ O_2$ = the oxygen concentration t = time of excitation

This ageing model has been affirmed according to empiric examinations. The intensity of fluorescence has been determinated with two known oxygen concentrations at two different times during the useful life of the layers wherein the offset error could be calculated from it with the following equation:

$$\text{Offset} = \frac{F(C\ O_{21}, t_1) * F(C\ O_{22}, t_2) - F(C\ O_{22}, t_1) * F(C\ O_{21}, t_2)}{F(C\ O_{21}, t_1) * F(C\ O_{22}, t_2) - F(C\ O_{22}, t_1) * F(C\ O_{22}, t_2)}$$

In practice, this method can be used for the basic adjustment of a device having an exemplary layer. For the basic adjustment, the measurements should be carried out within relatively great time intervals and repeatingly over a longer period, respectively, and with known oxygen concentrations the absolute values of which are widely spaced apart within a sense range as far as possible. The method which is favourable for the basic adjustment of a device, however, is not suitable for the determination of the offset (interfered error portion) of a new one, e.g. with the replacement of a layer the useful life of which is exceeded, for a new layer. On the other hand, measured values of both channels can be determined at each time on two known oxygen concentrations each. Thus, pairs of offset can be found which fulfill the requirement that the ratio of the measured values of both channels is constant with each of the known oxygen concentrations, and thus a common correction value is existing.

$$\frac{F_{MK}(C\ O_{21}) - \text{offset}_{MK}}{F_{KK}(C\ O_{21}) - \text{offset}_{KK}} = \frac{F_{MK}(C\ O_{22}) - \text{offset}_{MK}}{F_{KK}(C\ O_{22}) - \text{offset}_{KK}} = k(t)$$

Each solution of this equation is valid for the respective time. Though, the solution depending on ageing is to be found. If one selects for the correction channel, for example, an offset which has been determined with an exemplary layer at different ageing times, thus the offset of the measuring channel can be calculated beforehand.

$$\text{Offset}_{MK} = \frac{\begin{pmatrix} F_{MK}(C\ O_{21}) * (F_{KK}(C\ O_{22}) - \text{offset}_{KK}) - \\ F_{MK}(C\ O_{22}) * F_{KK}(C\ O_{21}) - \text{offset}_{KK} \end{pmatrix}}{\begin{pmatrix} F_{MK}(C\ O_{21}) * F_{KK}(C\ O_{22}) - \\ F_{MK}(C\ O_{23}) - F_{KK}(C\ O_{21}) \end{pmatrix}}$$

Originating from the basic adjustment of the system, thus pairs of values can be found which represent a good approximation of the real offsets.

On the pre-condition that the response time of the two channels is approximately equal, the quotient from the ageing depending portions of the measured values of the two channels merely depends on the excitation time but not on the oxygen concentration measured at this moment. Thus, the quotient is a time depending correction value k which can be calculated with the following equations $$k(t) = \frac{F_{MK}(C\ O_2, t) - \text{offset}_{MK}}{F_{KK}(C\ O_2, t) - \text{offset}_{KK}} = \frac{F'_{MK}(C\ O_2)}{F'_{KK}(C\ O_2)}$$

$$k(t) = \frac{A_{MK}(t) * F(C\ O_2)}{A_{KK}(t) * F(C\ O_2)} = \frac{A_{MK}(t)}{A_{KK}(t)}$$

With this correction value k the grade of ageing of the layer containing the fluorescent substance can be taken into consideration at any time.

On that occasion, the signal-to-noise ratio SNR of the correction channel according to the correction grade g is worse than that of the measuring channel such that applies $$SNR_{KK} = \frac{1}{\sqrt{g}} * SNR_{MK}$$

With a known correction value k correction of the test signals which are measured in the measuring channel can take place.

Ageing of the drift corrected signal (DS) corresponds to that of the correction channel, and it applies:

$$F_{DS}(C\ O_2, t) = \frac{F'_{MK}(C\ O_2, t)}{k(t)} = \frac{A_{MK}(t) * F(C\ O_2)}{\frac{A_{MK}(t)}{A_{KK}(t)}}$$

$$= A_{KK}(t) * F(C\ O_2)$$

With the aid of known ageing of the layer in the area and the layer, respectively, which is used for the measuring channel, and with the correction grade g being determined in a time depending manner the drift of the measuring channel as a result of ageing can be determined:

$$A_{kk} = A_{MK}\left(\frac{t}{g}\right)$$

A signal-to-noise ratio allowing for the ageing and longtime drift can be determined for the measuring channel with the predetermined correction value k according to the following equation:

$$SNR_{DS} = \frac{SNR_{MK}}{k}$$

such that the error occurring in the layer as a result of ageing is widely compensated since during the useful life of the used layers the correction values k are regularly allowed to be newly determined and taken into consideration with the corresponding compensation.

Moreover, it has been turned out that additional errors of measurement due to external light which impinges upon the layer containing fluorescent substances, and also passes on the optical detector and optical detectors, respectively, causes additional errors of measurement or the measuring sensitivity can be adversely affected by humidity during the determination of substance concentrations in gases as well.

In order to remove these adverse effects, a layer should be formed on the surface contacting the respective fluid medium of the layer containing the fluorescent substance, which is permeable at least to the substance to be detected. Such a coating should be light reflecting and/or hydrophobical.

The coating can be formed of known precious metals or compounds thereof. However, optically reflecting plastics, for example such ones which contain particles can also be employed.

The layer thickness can be selected up to 1000 nm.

For the determination of the oxygen concentration it has been proved as particularly advantageous to form a silver coating on the layer surface. For the determination of hydrogen concentrations a layer of palladium is particularly suitable. The coating should be formed preferably in the range of between 20 to 500 nm, wherein a uniform layer thickness above the layer should be met as far as possible. The coating should have a continuous thickness and should be formed in a homogenous manner at least in the areas which are used for the measurement and correction. The coating can be formed with the well-known methods in vacuum.

Subsequently, the invention will be explained in more detail according to an embodiment.

Herein

FIG. 1 shows in a diagrammatic form the construction of an embodiment of a device according to the invention with two light sources for the excitation of fluorescence, and one optical detector.

With the block diagram shown in FIG. 1 a layer containing a fluorescent matter is used, which is partitioned into two areas 1 and 2 being optically separated from each other. On the one side of this layer opposite the surface of the layer contacting the fluid medium, a so called reflexion measuring head 5 is located with this embodiment through which the guidance of light for excitation and measurement takes place. In such a reflexion measuring head 5 a plurality of optical fibers can be received by means of which the light for excitation of fluorescence in the layer of the two light sources used in this embodiment can be directed upon the two areas 1 and 2 of the layer, as indicated with the arrows. For example, the LED or laser diodes can be employed as light sources 3 and 4. The exciting light of the two light sources 3 and 4 is guided through optical filters 5 an 6 in order to guide as far as possible only the range of wavelength of light toward the layer by means of which fluorescence can be excited.

The fluorescence light of the two areas 1 and 2 of the layer can be directed again via the reflexion measuring head 5 through optical fibers via a third optical filter 8 upon an opticadetector 9 by means of which the intensity of the fluorescence can be measured. The optical filter 8 is designed for merely allow the light in the range of wavelength of the fluorescence to pass upon the opticadetector 9 (photodiode). With the electronic control 10 the two light sources 3 and 4 are switched on and switched off in a time-pulsed manner, wherein alternating switching on and off each is proper with this embodiment such that fluorescence is excited either in the area 1 or area 2 at the same times.

On that occasion, a measuring channel is irradiated with the light source 3, from which light is directed via the filter 6 through the reflexion measuring head 5 upon the area 1 of the layer, substantially longer over the useful life of the layer, and fluorescence is also excited accordingly, as being the case for the correction channel having the light source 4, filter 7 and area 2, such that during the useful life of the layer the excitation energy for the measuring channel and in particular for the area 1 is greater accordingly, and therefore ageing and long-time drift are greater accordingly.

The measured values detected with the optical detector 9 are allowed to be guided, if necessary, via an amplifier 11 to the electronic comparitive and correction value determination unit 12 in which the drift correction and reduction of the errors of measurement as described in the general part of the description in more detail are carried out by calculation.

The comparitive and correction value determination unit 12 is connected with the electronic control 10 in order to take into consideration an allocation of the test signals for the measuring and correction channels.

An input/output module can be connected to the electronic control 10 and the comparitive and correction value determination unit 12 by means of which the particular desired measuring procedure 5 can be selected, and the detected measured values can be outputted such that they can be made visible through a display or can also be fed to an electronic memory not shown, for example.

What is claimed is:

1. A device for optically measuring the concentrations of a substance in a fluid medium or the pH-value of the fluid medium, the device comprising:
   a layer containing a fluorescent substance to be detected, the layer comprising first and second separated areas;
   an exciting light source for directing an exciting light upon the first and second separated areas resulting in fluorescent light, a first excitation energy of the exciting light directed onto the first area differing with respect to a second excitation energy of the exciting light directed onto the second area over a determined time period, wherein differing excitation energies do not include differing wavelengths corresponding to the exciting light;
   at least one optical detector measuring the intensity, decay time or phase shift of the fluorescent light, the intensity, decay time or phase shift being locally and/or time separate for each area; and
   an electronic comparative and correction value determination unit, in which the measured values of intensity, decay time or phase shift are fed.

2. The device according to claim 1, further comprising a second exciting light source, the first and second exciting light sources adapted for being switched on and switched off for different excitation time intervals by an electronic time pulse control.

3. The device according to claim 1, further comprising a second optical detector, the fluorescent light from each area separately measurable by a separate optical detector.

4. The device according to claim 1, wherein the fluorescent light from each area are alternately directed upon the optical detector.

5. The device according to claim 1, further comprising a mechanically movable element between the exciting light source and the layer, the movable element temporarily stopping the exciting light in an electric or optoelectronic manner.

6. The device according to claim 5, wherein the movable element is a chopper.

7. The device according to claim 1, further comprising an optical filter temporarily inserted between the exciting light source and the layer.

8. The device according to claim 1, wherein the layer includes a coating permeable for the substance to be detected.

9. The device according to claim 8, wherein the coating is light reflecting.

10. The device according to claim 8, wherein the coating is selected from the group consisting of a precious metal, a metal compound, and a reflecting plastic.

11. The device according to claim 8, wherein the coating is selected from the group consisting of silver and palladium.

12. The device according to claim 8, wherein the coating has a thickness of about 1000 nm to about 20 mm.

13. A method for optically measuring the concentration of a substance contained in a fluid medium or the pH-value of the fluid medium, the method comprising:

providing a layer containing a fluorescent substance, the layer comprising separated first and second areas;

directing an exciting light for exciting of fluorescence upon the first and second areas;

selecting a first excitation energy of the exciting light directed onto the first area to be different with respect to a second excitation energy of the exciting light directed onto the second area over a determined time period, wherein differing excitation energies do not include differing wavelengths corresponding to the exciting light;

measuring values of fluorescence intensity, the fluorescence decay times or phase shifts, the fluorescence intensity, fluorescence decay times or phase shift being in a local and/or time separated manner for the first and second areas; and feeding the measured values to an electronic comparative and correction value determination unit.

14. The method according to claim 13, wherein directing an exciting light comprises directing a first exciting light source upon the first area and directing a second exciting light source upon the second area, the first and second exciting light sources having equal intensities, the excitation time of the first and second exciting light sources having differing intervals.

15. The method according to claim 14, further comprising alternating between directing the first and second light sources upon the first and second areas, respectfully, the excitation time of the first and second exciting light sources having differing intervals.

16. The method according to claim 14, wherein the excitation time of the first exciting light source is about 50% or less of the excitation time for the second exciting light source.

17. The method according to claim 14, further comprising stopping the direction of the first or second exciting light sources for a predetermined interval with a device selected from the group consisting of a movable element, a rotatable element, an electric element, an optoelectronic element, or an optical filter.

18. The method according to claim 14, further comprising determining a correction value k from the measured values of fluorescence intensity, fluorescence decay times or phase shifts for the area excited by an exciting light source for the least duration of excitation time.

* * * * *

UNITED STATES PATENT AND TRADEMARK OFFICE
CERTIFICATE OF CORRECTION

PATENT NO. : 6,914,677 B2  
DATED : July 5, 2005  
INVENTOR(S) : Mader et al.

It is certified that error appears in the above-identified patent and that said Letters Patent is hereby corrected as shown below:

Column 8,  
Line 64, "20 mm" should read -- 20 nm --.

Signed and Sealed this

Twenty-ninth Day of November, 2005

JON W. DUDAS  
*Director of the United States Patent and Trademark Office*